United States Patent [19]

Gasic et al.

[11] Patent Number: 5,385,885

[45] Date of Patent: Jan. 31, 1995

[54] INHIBITION OF SMOOTH MUSCLE CELL PROLIFERATION BY ANTISTASIN AND TICK ANTICOAGULANT PEPTIDE

[76] Inventors: Gregory P. Gasic, 12224 Caminito Del Mar, San Diego, Calif. 92130; Gabriel J. Gasic; Tatiana B. Gasic, both of 505 Hughes Rd., Gulph Mills, Pa. 19406

[21] Appl. No.: 730,487

[22] Filed: Jul. 16, 1991

Related U.S. Application Data

[63] Continuation-in-part of Ser. No. 515,859, Apr. 27, 1990, abandoned, which is a continuation-in-part of Ser. No. 144,453, Jan. 15, 1988, abandoned.

[51] Int. Cl.⁶ .................. C07K 7/10; C07K 15/08; A61K 37/02
[52] U.S. Cl. ...................... 514/12; 530/350; 530/858
[58] Field of Search .................. 530/350, 858; 514/12

[56] References Cited

U.S. PATENT DOCUMENTS

| | | | |
|---|---|---|---|
| 4,588,587 | 5/1986 | Gasic | 424/95 |
| 4,832,849 | 5/1989 | Cardin | 210/635 |
| 5,093,322 | 3/1992 | Bonin et al. | 530/350 |
| 5,106,833 | 4/1992 | Broze, Sr. et al. | 530/350 |

OTHER PUBLICATIONS

Moore, et al., Thromb. Diath. Haemorrh. 35:70 (1976).
Tuszynski, et al., J. Biol. Chem. 262:9718–9723 (1987).
Nutt, et al., J. Biol. Chem. 263:10162–10167 (1988).
Gasic, et al., Cancer Research 43:1633–1636 (1983).
Bajowski, et al., Proceeding of The American Association for Cancer Research 25:58, Abstract 330 (1984).
Gasic, et al., Cancer Research 44:5670–5676 (1984).
Gasic, et al., "Inhibition Of Metastasis And Cytotoxic Agent–Induced Metastasis Enhancement By Leech Salivary Gland Extracts", in Treatment of Metastasis: Problems and Prospects PROCEEDINGS, Hellman and Eccles, eds, Taylor and Francis, Lond and Philadelphia, pp. 275–278 (1985).
Waxman et al. (1990) Science 240:593–596.
Ross, The Harvey Lectures, Series 77, Academic Press, New York, N.Y. pp. 161–182 (1983).
Friedman, et al., J. Clin. Invest. 60:1191 (1977).
Harker, et al., N. Engl. J. Med. 291:537–543 (1974).
Harker et al., J. Clin. Invest. 58:731–741 (1976).
Brown et6 al., Amer. J. Cardiol. 49:968 (1982).
Ip et al., J. Am. College of Cardiology 15:1667–1687 (Jun. 1990).
Faxon et al., Am. J. of Cardiology 60:5B–9B (1987).
Powell et al., J. Am. College of Cardiology 17(6), Suppl B):173B–142B (May 1991).
Liu et al. Circulation 81:1089–1093 (1990).
Edelman, et al., Proc. Nat'l Acad. Sci. USA 87:1089–3777.
Nutt, et al., Arch. Biochem. Biophys 285:37–44 (1991).
Han et al., Gene 75: 47–57 (1989).
Neeper et al., J. Biol. Chem. 265:17746–17752 (1990).
Majesky, et al., Circulation Research 1987 61:293–300.
Sutton, et al., Circulation Research 1990 81:667–683.
Hanke, et al., Circulation Research 1990 67:651–659.
Becker, et al., Invest. Radiol. 1988 23:810–817.
Clowes, et al., Nature, vol. 265:625–626 (Feb. 17, 1977).
Schwartz, et al., Physiological Reviews, vol. 70, No. 4 pp. 1177–1209 (Oct. 1990).
Thomas et al., Annals New York Academy of Sciences, pp. 305–315.

Primary Examiner—Howard E. Schain
Assistant Examiner—Carol Salata
Attorney, Agent, or Firm—Woodcock Washburn Kurtz Mackiewicz & Norris

[57] ABSTRACT

The present invention provides methods for inhibiting smooth muscle cell proliferation, particularly smooth muscle cells present in blood vessel walls. A compound capable of inhibiting blood factor Xa is administered to the smooth muscle cells in an amount effective to inhibit proliferation of the cells. The compound capable of inhibiting blood factor Xa is preferably antistasin or tick anticoagulant peptide (TAP). In other aspects the present invention provides methods for treating atherosclerotic lesions and atherosclerosis, and methods of treating narrowing of the lumen of a blood vessel wherein the narrowing is caused at least in part by hyperplasia of smooth muscle cells in the wall of the blood vessel.

20 Claims, 2 Drawing Sheets

INHIBITION OF SMOOTH MUSCLE CELL PROLIFERATION BY ANTISTASIN AND TICK ANTICOAGULANT PEPTIDE

REFERENCE TO RELATED U.S. PATENT AND APPLICATION

The present application is related to U.S. Pat. No. 4,588,587 issued May 13, 1986 to Gabriel J. Gasic. The present application is a continuation-in-part of co-pending U.S. application Ser. No. 07/515,859 filed Apr. 27, 1990, now abandoned which is in turn a continuation-in-part of co-pending U.S. application Ser. No. 07/144,453 filed Jan. 15, 1988, now abandoned entitled "Protein Having Anticoagulant and Antimetastatic Activity", the disclosures of both of which are hereby incorporated by reference.

FIELD OF THE INVENTION

The present invention relates to the field of methods for inhibiting cell proliferation. More particularly the present invention relates to the use of proteins derived from leeches or ticks as agents for inhibiting smooth muscle cell proliferation, treating atherosclerosis or inhibiting smooth muscle cell proliferation after balloon angioplasty or other surgical procedure.

BACKGROUND OF THE INVENTION

Atherosclerosis has been known to be an important disease in humans since the beginning of recorded medical history. However, it was not until the early portion of the twentieth century that it became clearly recognized that the syndrome of myocardial infarction was associated with coronary atherosclerosis and thrombosis. Epidemiological studies during the 1970's demonstrated that cardiovascular disease is the cause of approximately 50% of all deaths in western civilization. Recent observations suggest that there has been a decline in mortality from coronary heart disease associated with a reduction in the incidence of coronary atherosclerosis. Despite the apparent reduction in mortality from coronary heart disease, atherosclerosis remains an important cause of death in the United States.

Since the late 1970's, coronary balloon angioplasty has become an accepted form of therapy for coronary artery disease. Unfortunately, in about a third of patients undergoing this treatment, intimal hyperplasia occurs and vascular restenosis appears within about six months after surgery. Proliferation of smooth muscle cells in the walls of blood vessels treated by balloon angioplasty followed by restenosis of the blood vessel is recognized as a serious drawback of balloon angioplasty. In addition to restenosis of blood vessels after balloon angioplasty, smooth muscle cell proliferation leading to stenosis of blood vessels is also a serious drawback of percutaneous transluminal coronary angioplasty and is associated with accelerated coronary atherosclerosis after cardiac transplantation. Consequently, there is a great need for agents and treatments to reduce smooth muscle cell proliferation found in blood vessels after these types of surgical procedures.

Antistasin is a protein found in salivary gland extracts of the Mexican leech *Haementeria officinalis* having antimetastatic and anticoagulant activity. Tuszynski et al. (1987) J. Biol. Chem. 262: 9718–9723 report isolation and characterization of antistasin from the salivary glands of the Mexican leech *Haementeria officinalis*. Nutt et al. (1988) J. Biol. Chem. 263: 10162–10167 report the amino acid sequence of antistasin. Antistasin possesses 119 amino acid residues and is blocked at its amino terminus by the presence of a pyroglutamic acid residue and has an unusually high cysteine content, with 20 cysteine residues. The primary structure of antistasin shows no homology to hirudin, a 65-residue anticoagulant protein from the medicinal leech, *Hirudo medicinalis*. Antistasin contains significant internal homology where a 2-fold internal repeated structure is observed. At least four isoforms of antistasin have been identified in leech salivary gland extracts by high performance liquid chromatography, and partial amino acid sequence or analysis of these isoforms indicates they differ by one or two amino acid residues.

U.S. Pat. No. 4,588,587 issued May 13, 1986 to Gasic discloses a method for treating a patient to inhibit metastasis of malignant cells by administering to a patient a therapeutically effective amount of a leech salivary gland extract. The patent also discloses a method for preparing the salivary gland extract.

Gasic et al (1983) Cancer Research 43: 1633–1636 reports the inhibition of lung tumor colonization by leech salivary gland extracts.

Bajowski et al (1984) Proceeding of the American Association for Cancer Research 25: 58, abstract 230 reports the inhibition of murine tumor cathepsin B by leech salivary gland extracts from *Haementeria officinalis*.

Gasic et al. (1984) Cancer Research 44: 5670–5676 reports inhibition of cyclophosphamide- and radiation-induced artificial metastasis enhancement by an extract of the salivary glands from *Haementeria officinalis*.

Gasic et al. "Inhibition of metastasis and cytotoxic agent-induced metastasis enhancement by leech salivary gland extracts" in Treatment of metastasis: Problems and prospects PROCEEDINGS, Hellman and Eccles, eds, Taylor and Francis, London and Philadelphia, 1985, pp. 275–278, reports the inhibition of metastasis formation and prevention of enhancement of metastases induced by iatrogenic agents by an extract from the salivary glands of the leech *Haementeria officinalis*.

Tick anticoagulant peptide (TAP) is a sixty amino acid protein isolated from the tick *Ornithodoris moubata* which is a highly specific inhibitor of blood coagulation factor Xa, Waxman et al. (1990) Science 240: 593–596. Tick anticoagulant peptide contains six cysteine residues, and exhibits limited homology to the Kunitz class of inhibitor. Tick anticoagulant peptide exhibits a high degree of specificity for factor Xa, and is reported to have no effect on Factor VIIa, kallikrein, trypsin, chymotrypsin, thrombin, or several other factors in the blood coagulation cascade, (Waxman et al., supra).

SUMMARY OF THE INVENTION

The present invention provides methods for inhibiting smooth muscle cell proliferation, particularly smooth muscle cells present in blood vessel walls. A compound capable of inhibiting blood factor Xa is administered to the smooth muscle cells in an amount effective to inhibit proliferation of the cells. In preferred embodiments of the method of the invention, the compound capable of inhibiting blood factor Xa is antistasin or tick anticoagulant peptide (TAP). In another aspect the present invention provides methods for treating atherosclerotic lesions and atherosclerosis. A further aspect of the invention provides methods of treating narrowing of the lumen of a blood vessel wherein the narrowing is due at least in part to hyperplasia of smooth muscle cells in the wall of the blood vessel comprising administering to a blood vessel having such narrowing of the lumen a compound capable of inhibiting blood factor Xa in an amount effective to inhibit proliferation of smooth muscle cells in the blood vessel wall to thereby increase the size of the lumen of the blood vessel. This invention is more particularly pointed out in the appended claims and described in its preferred embodiments in the following description.

DETAILED DESCRIPTION OF THE INVENTION

Antistasin is a 119-amino acid protein isolated from the salivary glands of the Mexican leech *Haementeria officinalis*. The amino acid sequence reveals that it is a highly disulfide-bonded polypeptide, which shows no overall sequence similarity to any known peptide. Tick anticoagulant peptide is a 60-amino acid peptide isolated from extracts of the soft tick *Ornithodoros moubata*. Tick anticoagulant peptide is a potent inhibitor of blood factor Xa (Waxman et al. supra).

Applicants have found that antistasin markedly decreases the release of endothelial cell derived mitogens upon stimulation with blood clotting factor Xa as compared with controls. Similarly, antistasin also diminishes release of mitogens (i.e., compounds that induce or stimulate cell growth and/or division) due to stimulation of endothelial cells with platelet derived growth factor (PDGF), a smooth muscle cell mitogen. Antistasin may also block the release of mitogens from endothelial cells that are mediated by other growth factors. This inhibitory activity may be mediated by antistasin's inhibition of protease activity (e.g. Xa) or by inhibition of binding. By blocking the release of growth factors from endothelial cells, antistasin is expected to diminish intimal smooth muscle proliferation and possibly the accumulation of lipid laden macrophages and smooth muscle cells which would otherwise result in vascular occlusion. Platelet derived endothelial cell growth factor (PDECGF) would, however, still be free to act on endothelial cells in order to repopulate a region in a damaged vessel.

As used herein, the terms attenuation of atherogenesis or attenuation of atherosclerotic lesions includes the reduction or inhibition of proliferation of smooth muscle cells at the sites of vascular lesions.

Applicants have also found that compounds capable of inhibiting blood factor Xa, preferably antistasin or tick anticoagulant peptide, are effective for inhibiting proliferation of smooth muscle cells. Applicants have further found that antistasin and tick anticoagulant peptide can inhibit DNA synthesis in smooth muscle cells.

Additionally, Applicants have found that protein S is a powerful stimulator of smooth muscle cell proliferation. Smooth muscle cell proliferation induced by 10 mM human protein S was greater than the amount of smooth muscle cell proliferation induced by 50 mM bovine factor Xa. Applicants further found that protein S induced smooth muscle cell proliferation was significantly inhibited by antistasin and tick anticoagulant peptide.

By inhibiting proliferation of smooth muscle cells, antistasin and tick anticoagulant peptide are expected to be useful for reducing excessive smooth muscle cell proliferation associated with surgical treatments such as balloon angioplasty, percutaneous transluminal coronary angioplasty and accelerated coronary atherosclerosis after cardiac transplantation.

The present invention thus provides a method of inhibiting proliferation of smooth muscle cells, comprising administering to such cells a compound capable of inhibiting blood factor Xa in an amount effective to inhibit proliferation of the smooth muscle cells. Another aspect of the invention provides a method of inhibiting DNA synthesis of smooth muscle cells, comprising administering to the cells a compound capable of inhibiting blood factor Xa in an amount effective to inhibit DNA synthesis of the smooth muscle cells. A further aspect of the present invention provides a method of treating an atherosclerotic lesion wherein the lesion comprises smooth muscle cells, comprising administering to the atherosclerotic lesion a compound capable of inhibiting blood factor Xa in an amount effective to inhibit proliferation of the smooth muscle cells in the atherosclerotic lesion. Another aspect of the invention provides a method of treating smooth muscle cell proliferation in atherosclerotic lesion of a mammal having atherosclerosis comprising administering to such mammal compound capable of inhibiting blood factor Xa in an amount effective to inhibit proliferation of smooth muscle cells. An additional aspect of the invention provides a method of treating narrowing of the lumen of a blood vessel wherein narrowing is caused at least in part by hyperplasia (i.e. proliferation) of smooth muscle cells in the wall of the blood vessel or is the result at least in part of hyperplasia of smooth muscle cells in the wall of the blood vessel, particularly in response to stretching of the blood vessel wall during balloon angioplasty, or other injury to the blood vessel wall during surgical procedures such as angioplasty, which comprises administering to a blood vessel having such narrowing of the lumen a compound capable of inhibiting blood factor Xa in an amount effective to inhibit proliferation of smooth muscle cells in the blood vessel wall to thereby increase the size of the lumen of the blood vessel. For use in the methods of the present invention, the compound capable of inhibiting blood factor Xa, or inhibiting DNA synthesis of smooth muscle cells, is preferably antistasin, tick anticoagulant peptide, a combination of antistasin and tick anticoagulant peptide, or at least one fragment of antistasin or tick anticoagulant peptide capable of inhibiting smooth muscle cell proliferation. More preferably the compound capable of inhibiting blood factor Xa is antistasin or tick anticoagulant peptide. As used herein the phrase "inhibition of smooth muscle cell proliferation" refers to reduction in the amount of smooth muscle cell growth and division in comparison with the amount of cell growth and division of smooth muscle cells stimulated to grow and divide by stimulatory compounds such as blood factor Xa.

In studies on the structure of atherosclerotic lesions, Ross, R., The Harvey Lectures, Series 77, Academic Press, New York, N.Y. (1983), pp. 161–182, found that most of the human atherosclerotic lesions examined had the appearance of classical fibrous plaques in which the fibrous cap that characteristically overlies the fibrous plaque consists of essentially only one cell type—smooth muscle. Each of these smooth muscle cells appeared to lie in a lacuna-like space that consisted of a multilamella arrangement of basement membrane, interspersed with proteoglycan, surrounded by small, poorly developed elastic fibers. The smooth muscle cell lying in the center of each of these lacuna-like spaces was large, flat, and disk-shaped. Each of the "lacunae" appeared to be surrounded by a dense fibrous connective tissue containing numerous bundles of collagen fibrils, proteoglycan, and elastic fibers. Beneath this fibrous cap was a highly cellular lesion consisting of two clearly identifiable cell types: smooth muscle and macrophages. In many instances, both of these cells were seen to contain numerous lipid droplets, which were generally more numerous in the macrophage than in the smooth muscle cells. In many instances the deposits of lipid were so extensive that they modified cell morphology. Deep beneath this proliferative zone there was often a great deal of cell and lipid debris intermixed with cholesterol crystals. The lesions of human atherosclerosis thus contain three biologically important elements. (a) There are large numbers of smooth muscle cells mixed with varying number of macrophages. (b) In many regions of the lesion these cells are surrounded by an extensive dense connective tissue that must have been synthesized, in most cases, by the smooth muscle cells. (c) These smooth muscle proliferative, connective tissue-rich lesions also contain varying amounts of intercellular and extracellular lipid. These three phenomena can occur in varying amounts and therefore provide lesions of atherosclerosis that can be quite different from one another in appearance, based on the relative amounts of smooth muscle proliferation and connective tissue and the extent of lipid that has accumulated in the lesions.

Ross, R., The Harvey Lectures, Series 77, Academic Press, New York, N.Y. (1983), pp. 161–182 and others have postulated that injury to the endothelium of blood vessels is responsible for atherosclerotic lesions. As a response to injury a number of cyclic events may occur. In the regression cycle injury to the endothelium occurs as separations between endothelial cells or by frank desquamation of the endothelium in which both adherence of platelets and of monocyte/macrophages may occur. If platelet adherence occurs, aggregation and release of platelet contents (PDGF, PDECGF) may also take place at such sites, whereas monocytes may go on to enter the tissue either at sites of desquamation or between endothelial cells. These interactions may be followed by migration of smooth muscle cells from the media into the intima of the blood vessel, and proliferation of these and possible preexisting intimal smooth muscles cells in response to mitogens released from platelets and other cells. At the end of the regression cycle, if the lesion is a single event and endothelial integrity is restored, the remnant of the proliferation response may simply be manifest as a somewhat thickened intima. If repeated or chronic injury occurs as may happen in hyperlipidemia or after other forms of continuing injury, both lipid accumulation and continued smooth muscle proliferation may occur. After recurrent sequences of proliferation and regression, complicated lesions may develop that may go on to calcify. This continued cyclic progression could eventually produce the clinical sequelae of thrombosis and infarction.

Moore et al. (1976) Thromb. Diath. Haemorrh. 35: 70 have shown that atherosclerosis induced in rabbits by a chronic indwelling catheter can be prevented if the rabbits were made thrombocytopenic with an antiplatelet serum. Similarly, Friedman et al. (1977) J. Clin. Invest. 60: 1191 demonstrated in rabbits that lesions induced with an intraarterial balloon catheter can be prevented if the animals are thrombocytopenic. In baboons having chronic homocystinemia, extensive lesions of atherosclerosis developed, associated with overlying areas of endothelial desquamation, when the baboons were homocystinemic for three months. The homocystinemic baboons had markedly shortened platelet survivals. When these baboons were treated with antiplatelet agents, such as doses of dipyridamole sufficiently high to prevent platelet adherence and release, smooth muscle proliferative responses were prevented (Harker et al. (1974) N. Engl. J. Med. 291: 537–543; Harker et al. (1976) J. Clin. Invest 58: 731–741).

The results of a study in humans by Brown et al. (1982) Amer. J. Cardiol. 49: 968 suggest that the observations made in experimental animals concerning the role of the platelets in atherogenesis may be important. PDGF is released from platelets and was believed to be the principal factor involved in smooth muscle cell proliferation central to atherogenesis. A statistically significant number of the patients treated with the antiplatelet regimen demonstrated a decreased incidence of new lesions of atherosclerosis as compared with patients on placebo.

Cellular proliferation as a result of endothelial injury narrows the lumen of a blood vessel acting as a nidus for the accumulation of lipids, eventually forming a plaque, and ultimately occluding the blood vessel. By inhibiting or avoiding cellular proliferation with the use of antistasin during the healing process of blood vessels, occlusion of the blood vessel should be reduced or eliminated.

A situation commonly encountered following balloon angioplasty is reocclusion of the blood vessel. Reclosing of the blood vessel is thought to be due to injury to the endothelial cells of the blood vessel during angioplasty, or during inflation of the balloon catheter. During healing of the blood vessel after surgery, smooth muscle cells proliferate faster than endothelial cells narrowing the lumen of the blood vessel, and starting the atherosclerotic process anew. In recent years, smooth muscle cell proliferation has been recognized as a major clinical problem limiting the long-term efficacy of percutaneous transluminal coronary angioplasty and balloon angioplasty. In efforts to prevent restenosis of the treated blood vessel, agents that can reduce or prevent excessive proliferation of smooth muscle cells have been the object of much research. The occurrence and effects of smooth muscle cell proliferation after these types of surgery have been reviewed, for example, in Ip et al. (June 1990) J. Am. college of Cardiology 15: 1667–1687, and Faxon et al. (1987) Am. J. of Cardiology 60: 5B–9B. Various platelet inhibitors and inhibitors of platelet-derived growth factor have been tested experimentally for their ability to reduce smooth muscle cell proliferation. Powell et al. (May 1991) J. Am. College of Cardiology 17(6,Suppl B): 137B–142B reported that the angiotensin-converting enzyme inhibitor cilazapril specifically inhibits the smooth muscle cell proliferative response to balloon catheter injury in a rat model of balloon catheterization. Liu et al. (1990) Circulation 81: 1089–1093 reported that trapidil (triazolopyrimidine) which possesses activity against platelet-derived growth factor-induced cellular proliferation in vitro, significantly increased luminal area and reduced intimal thickness in atherosclerotic rabbit iliac arteries after balloon angioplasty. Edelman et al. (1990) Proc. Nat'l. Acad. Sci. USA 87: 3773–3777 reported that site-delivered heparin effectively diminished proliferation of smooth muscle cells after balloon catheterization of rat carotid arteries.

Administration of the compounds of the invention is expected to reduce or avoid excessive smooth muscle cell proliferation after balloon angioplasty or percutaneous transluminal coronary angioplasty leading to restenosis of the blood vessel, thus reducing the likelihood of a reoccurrence of the condition.

Antistasin may be prepared according to several methods, such as the methods disclosed in U.S. Pat. No. 4,588,587 issued May 13, 1986 to Gasic; copending U.S. patent application Ser. No. 144,453 filed Jan. 15, 1988; and Nutt et al. (1988) J. Biol. Chem. 263: 10162–10167; the disclosures of each of the foregoing are hereby incorporated by reference as if fully set forth herein. Each of the foregoing disclose methods of purifying antistasin from the salivary glands of the Mexican leech *Haementeria officinalis*. At the present time, however, methods of purifying antistasin that result in a purer product are preferred for therapeutic purposes, such as the method in copending U.S. application Ser. No. 144,453 or Nutt et al. supra. A preferred method for the preparation of antistasin as disclosed in Nutt et al. is presented in Example 1. Recombinant antistasin is also suitable for use in the methods of the invention and may be preferable in some circumstances. Recombinant antistasin may be prepared, for example, according to the method of Nutt et al. (1991) Arch. Biochem. Biophys. 285: 37–44, and Han et al (1989) Gene: 75: 47–57; the disclosures of both of these publications is hereby incorporated by reference.

Tick anticoagulant peptide may be prepared from the tick *Ornithodoros moubata* according to methods known the art such as the method of Waxman et al. (1990) Science 248: 593–596, the disclosures of which are hereby incorporated by reference. Tick anticoagulant peptide may also be prepared by recombinant DNA techniques according to the method of Neeper et al. (1990) J. Biol. Chem. 265: 17746–17752, the disclosures of which are hereby incorporated by reference.

Derivatives of antistasin and tick anticoagulant peptide having atherosclerotic attenuation activity are also within the scope of the invention. Such derivatives include fragments of antistasin and tick anticoagulant peptide having atherosclerotic attenuation activity. Antistasin, tick anticoagulant peptide, or fragments thereof modified by the addition of therapeutic, or diagnostic compounds, and antistasin, tick anticoagulant peptide, or fragments thereof modified by the addition or deletion of amino acids are also within the scope of the invention. Fragments of antistasin and tick anticoagulant peptide capable of inhibiting smooth muscle cell proliferation are also within the scope of the invention. Such fragments may be selected by cleaving antistasin or tick anticoagulant peptide into discrete peptides, or synthesizing the discrete peptides by solid phase peptide synthesis, such as Merrifield solid phase peptide synthesis, and testing the resulting peptides in the assay described herein for inhibition of smooth muscle cell proliferation in Example 4, or any other assay or animal model for testing inhibition of smooth muscle cell proliferation. Antistasin, tick anticoagulant peptide, or portions or fragments thereof prepared by any method including purification from leeches or other organism, chemical synthesis, recombinant DNA techniques and any combination of these methods is within the scope of the invention. Isoforms of antistasin are also within the scope of the invention. As disclosed in Nutt et al., supra, several isoforms of antistasin differing by one or two amino acids have been found with antistasin in extracts of salivary glands. These isoforms cross-react with antibodies raised to antistasin. As purification of antistasin is initiated currently from pooled gland extracts of 200–1,000 leeches, the possibility exists that the isoforms of antistasin represent polymorphisms within the species. Similarly, tick anticoagulant peptide purified from pooled extracts of individual ticks may also be present as isoforms due to polymorphisms within the species.

For use in the methods of the present invention, the compound capable of inhibiting blood factor Xa may be administered to mammals, which will generally be a human patient, in combination with a pharmaceutically acceptable carrier or diluent such as water, a saline solution, or physiologically acceptable buffer. The compound may be administered in combination with other compounds capable of inhibiting blood factor Xa, such as, for example, a combination of antistasin and tick anticoagulant peptide, or a combination of antistasin and a fragment thereof capable of inhibiting smooth muscle cell inhibition. The compound capable of inhibiting blood factor Xa may also be administered in combination with other compounds used in the treatment of atherosclerosis such as total parenteral nutrition and fibrinolytic therapy. The compound capable of inhibiting blood factor Xa may be administered in combination with balloon angioplasty, or other forms of surgical treatment. The compound is preferably administered orally, or by intravenous or intraarterial injection, however, other routes of administration, such as topical administration during surgery may also be suitable. The amount of the compound administered will vary according to such factors as the age, sex and weight of the patient, the coadministration of other therapeutic agents, and the use of other treatments in combination with administration of the compound capable of inhibiting blood factor Xa. The compound is administered to the patient suffering from atherosclerotic lesion or for attenuation of the atherosclerotic process for a length of time effective to reduce or avoid smooth muscle cell proliferation. In other aspects of the invention, the compound is administered for a length of time sufficient to reduce or avoid smooth muscle cell proliferation. The compound capable of inhibiting blood factor Xa may be given as a single dose, or as divided doses. Eventually, the gene for antistasin, within a suitable vector, may be introduced into healthy human endothelial cells obtained from the patient, and then be placed within the damaged vessel of the same patient. Additionally, administration of the compound capable of inhibiting blood factor Xa may be accomplished by site-directed administration by combining the compound with a suitable matrix and implanting the matrix at or near the surgical site.

EXPERIMENTAL

EXAMPLE 1

Purification of Antistasin

The following procedure for the purification of antistasin is from Nutt et al., supra.

An extract of the salivary gland of the Mexican leech *Haementeria officinalis* was prepared by extracting the dissected anterior and posterior glands at 4° C. by sonication in a buffer of 20 mM 9-(2-hydroxyethyl)-1-piperazineethanesulfonic acid (HEPES), pH 7.8, containing 10 mM $CaCl_2$. The sonicated material was centrifuged at 8,500×g for 20 minutes, and the supernatants were pooled and centrifuged at 100,000×g for 1 hour. The resulting protein suspension was frozen at −70° C. until needed.

Heparin-agarose (Sigma Chemical Co., St. Louis, Mo.) chromatography of 50-ml batches of this suspension was performed on a 5-ml column equilibrated with 20 mM HEPES, pH 7.8, and eluted stepwise with 0.35M NaCl in 20 mM Tris, pH 8.7, and 0.55M NaCl in 20 mM Tris, pH 8.7. Anticoagulant activity eluted in the latter fraction.

The second fraction having anticoagulant activity was run by high performance liquid chromatography (HPLC) on a C4 Vydac protein column in 100 μl (about 80 μg of protein) batches with a 30 minute gradient of 15–30% isopropyl alcohol in 0.1% trifluoroacetic acid at a flow rate of 0.5 ml/min.

EXAMPLE 2

Antagonism by Antistasin (ATS) of the Release of Mitogens From Endothelial Cells Stimulated With Factor Xa Confluent primary cultures or subcultures (passages 1 and 2) of human venous endothelial cells (EC) were cultured in serum-free Dulbecco's Minimal Essential Medium (DMEM)+0.1% bovine serum albumin (BSA) in the presence of human or bovine factor Xa(1 nM) (Sigma Chemical Co., St. Louis, Mo.), antistasin (ATS) (0.5–5.0 nM), or both. Control cultures were untreated or received 2 ng/ml platelet-derived growth factor (PDGF) (Sigma Chemical Co., St. Louis, Mo.). After 16 hours incubation at 37° C., the conditioned media (CM) from the test and control cell cultures were collected and tested for mitogenic activity (MIT) using confluent NIH 3T3 cells (CCL 163, American Type Culture Collection, Rockville, Md.).

Primary cultures of EC derived from umbilical cord veins were prepared and grown according to a protocol provided to by Dr. Gwendolyn Stewart (Temple University Thrombosis Center, Phila., Pa.). After washing the lumen of the vein twice with DMEM, EC were dissociated with a solution containing 0.05% trypsin and 0.1% collagenase. Thirty minutes later, the venous content and the perfused DMEM (35 ml) was collected into a fifty ml centrifuge tube containing 3.5 ml of bovine serum and the mixture spun at 900 rpm for 10 minutes. The supernate was discarded and the cell pellet resuspended in 3.0 ml DMEM containing 20% fetal bovine serum (FBS) (heat inactivated at 56° C. for 30 minutes), 90 μg heparin per ml, 5 μg fibronectin per ml, and 60 μg endothelial growth factor per ml (cDMEM), and seeded into 35 mm tissue culture dishes. After 24 hours of incubation at 37#C, 5% $CO_2$, the culture was washed 3–4 times with DMEM and incubated 2–4 days until the cells were confluent. The monolayers were washed with phosphate buffered saline (PBS) and cultured in DMEM with 0.1% BSA in the presence and absence of 1 nM factor Xa, 5 nM antistasin, or a mixture of both. As positive and negative controls, separated monolayers were incubated with the medium plus 2 ng/ml PDGF or with the medium alone. After 16 hours of incubation at 37° C., conditioned media (CM) were collected, centrifuged at 4000×g for 10 minutes, and the supernate was collected and stored at 4° C. until use. The mitogenic activity of the CM was tested by measuring the incorporation of [$^3$H] thymidine into cultures of Balb 3T3 cells. For this purpose, wells were seeded with 2×10$^4$ 3T3 cells suspended in 1 ml DMEM with 10% FBS. Once confluent (5–7 days of culture), CM were added and cells incubated for 18 hours at 37° C. after which cultures were washed with warm DMEM, tritiated thymidine added (1 μCi/ml) and cells incubated for 4 hours at 37° C. After removing the medium, the culture was washed twice with cold 5% trichloroacetic acid (TCA), and lysed with 0.8 ml 0.25M NaOH. The lysate was transferred to vials with scintillation fluid and radioactivity monitored in a beta radiation counter.

One unit of mitogenic activity is defined as the mitogenic activity induced by 2 ng/ml PDGF. Each assay was performed in triplicate and the standard deviation was less than 10%. Antistasin treatment of 3T3 cells has no significant effect on their proliferation.

Table 1 shows the results of these experiments. The mitogenic activity of 3T3 cells is significantly reduced when cultured in the presence of both FXa and ATS.

Using several different doses of antistasin (0.5–10 nM), it was observed that antistasin blocks the release of mitogens from endothelial cells. These mitogens stimulate the proliferation of 3T3 fibroblasts which resemble the smooth muscle cells that proliferate in atherosclerotic lesion.

TABLE 1

| EC TREATMENT | MITOGENIC UNITS | | | |
|---|---|---|---|---|
| | EXP 1 | EXP 2 | EXP 3 | EXP 4 |
| None | 0.75 | 0.52 | 0.63 | 0.45 |
| PDGF | 1.00 | 1.00 | 1.00 | 1.00 |
| FXa | 1.01 | 0.88 | 0.90 | 0.68 |
| ATS | 0.74 | 0.42 | 0.70 | 0.36 |
| FXa + ATS | 0.86 | 0.45 | 0.79 | 0.50 |

EXAMPLE 3

Antagonism By Antistasin (ATS) Of The Release Of Mitogens From Endothelial Cells Stimulated With Platelet-Derived Growth Factor (PDGF)

Confluent primary cultures or subcultures (passages 1 and 2) of human venous endothelial cells were cultured in serum-free Dulbecco's Minimal Essential Medium (DMEM)+0.1% bovine serum albumin (BSA) in the presence of platelet-derived growth factor (PDGF) (2 ng/ml), antistasin (ATS) (5.0–10 nM), or both. Control cultures were untreated or received 2 ng/ml PDGF. After 16 hours incubation at 37° C., conditioned media (CM) from the test and control cell cultures were collected and tested for mitogenic activity (MIT) using confluent NIH 3T3 cells (CCL 163, American Type Culture Collection, Rockville, Md.).

Primary cultures of EC derived from umbilical cord veins were prepared and grown according to a protocol provided to by Dr. Gwendolyn Stewart (Temple University Thrombosis Center, Phila., Pa.). After washing the lumen of the vein twice with DMEM, EC were dissociated with a solution containing 0.05% trypsin and 0.1% collagenase. Thirty minutes later, the venous content and the perfused DMEM (35 ml) was collected into a fifty ml centrifuge tube containing 3.5 ml of bovine serum and the mixture spun at 900 rpm for 10 minutes. The supernate was discarded and the cell pellet resuspended in 3.0 ml DMEM containing 20% fetal bovine serum (FBS) (heat inactivated at 56° C. for 30 minutes), 90 μg heparin per ml, 5 μg fibronectin per ml, and 60 μg endothelial growth factor per ml (cDMEM), and seeded into 35 mm tissue culture dishes. After 24 hours of incubation at 37#C, 5% $CO_2$, the culture was washed 3-4 times with DMEM and incubated 2-4 days until the cells were confluent. The monolayers were washed with phosphate buffered saline (PBS) and cultured in DMEM with 0.1% BSA in the presence and absence of 2 ng/ml PDGF, 5 nM antistasin, or a mixture of both. As positive and negative controls, separated monolayers were incubated with the medium plus 2 ng/ml PDGF or with the medium alone. After 16 hours of incubation at 37° C., conditioned media (CM) were collected, centrifuged at 4000×g for 10 minutes, and the supernate was collected and stored at 4° C. until use. The mitogenic activity of the CM was tested by measuring the incorporation of [$^3$H] thymidine into cultures of Balb 3T3 cells. For this purpose, wells were seeded with $2 \times 10^4$ 3T3 cells suspended in 1 ml DMEM with 10% FBS. Once confluent (5-7 days of culture), CM were added and cells incubated for 18 hours at 37° C. after which cultures were washed with warm DMEM, tritiated thymidine added (1 μCi/ml) and cells incubated for 4 hours at 37° C. After removing the medium, the culture was washed twice with cold 5% trichloroacetic acid (TCA), and lysed with 0.8 ml 0.25M NaOH. The lysate was transferred to vials with scintillation fluid and radioactivity monitored in a beta radiation counter.

One unit of mitogenic activity is defined as the mitogenic activity induced by 2 ng/ml PDGF. Each assay was performed in triplicate and the standard deviation obtained was less than 10%.

As shown in Table 2, antistasin decreased the release of endothelial derived mitogens upon treatment with PDGF (2 ng/ml).

TABLE 2

| EC TREATMENT | MITOGENIC UNITS | | |
|---|---|---|---|
| | EXP 1 | EXP 2 | EXP 3 |
| None | 0.53 | 0.61 | 0.45 |
| PDGF | 1.00 | 1.00 | 1.00 |
| PDGF + ATS | 0.55 | 0.73 | 0.78 |

These experiments demonstrate that antistasin blocks the release of mitogens from endothelial cells when stimulated with coagulation factor Xa or PDGF. These mitogens cause the proliferation of 3T3 fibroblasts which are very similar to smooth muscle cells. Factor Xa is produced by the activation of the clotting cascade, an event which occurs upon vascular injury. PDGF is released from platelets during injury which occurs in atherosclerotic lesions. Antistasin would act to reduce the injury response by decreasing mitogen release from platelets (activated by thrombin) and from endothelial cells. By decreasing mitogen release, antistasin would permit the regrowth of endothelial cells in a region of damage but inhibit proliferation of smooth muscle cells which would consequently prevent vascular occlusion.

EXAMPLE 4

Effect of Blood Coagulation Factors on Mitogenic Activity of Smooth Muscle Cells Recombinant antistasin and recombinant tick anticoagulant peptide (TAP) were provided by Drs. C. Dunwiddie, G. P. Vlasuk and P. A. Friedman, Merck Sparpe & Dohme Research Labs, West Point, Pa. Recombinant antistasin was prepared according to the method of Nutt et al. (1991) Arch. Biochem. Biophys. 285: 37-44, the disclosures of which are hereby incorporated by reference. Recombinant TAP was prepared according to the method of Neeper et al. (1990) J. Biol. Chem. 265: 17746-17752, the disclosures of which are hereby incorporated by reference.

Primary smooth muscle cell cultures were prepared from the thoracic and abdominal aorta of 2-3 month old Wistar rats essentially using the procedure of Reilly, C. F. (1990) J. Cell Physiol. 142,342 (1990). After removing as much fat and adherent adventitia as possible with scissors and forceps, the tissue was finely minced, enzymatically dissociated with successive 37° C. incubations in HBSS containing collagenase (Sigma, 0.5 mg/ml for 15 min.), then elastase (Sigma, 0.125 mg/ml for 30 min.) and again collagenase (60 min.). The dissociated cells had a spindle shaped morphology. Cells were grown in Dulbecco's Minimal Essential Medium (DMEM) containing 10% fetal bovine serum (FBS) with antibiotics. At confluence, the cells exhibit overlapping. Using a monoclonal antibody to alpha actin (Sigma Chemical Company, St. Louis, Mo.), about 60-80% (preparation dependent) of these confluent cells stained positive for this smooth muscle cell marker. After 10 days in culture, the cells were dissociated with trypsinethylene diamine tetraacetate (EDTA), split 1:10 and subcultured in the above medium. At confluence the cells were transferred to DMEM containing 0.1% FBS for a 24 hour period before using them for assay. All smooth muscle cells used in these studies were from passages 1-4. Simian Virus 40 (SV-40) transformed smooth muscle cell line was provided by Dr. C. F. Reilly, Merck Sharpe & Dohme Research Laboratories, West Point, Pa.

The prepared rat smooth muscle cells were seeded in Falcon 24 multiwell plates ($10^5$ cells/well) and cultured at 37° C., in a 5% $CO_2$ atmosphere in 1 ml DMEM containing 10% FBS. At confluence (3-4 days), the cultures are washed twice with DMEM and incubated for 24 hours in DMEM containing 0.1% bovine serum albumin (BSA, Sigma Chemical Co., St Louis, Mo., RIA grade) (control), which is the buffer used to dissolve the coagulation factors, or 0.1 nM platelet-derived growth factor-BB (recombinant PDGF-BB, a gift from Dr. Pablo Valenzuela, Chiron, Emeryville, Calif.), or 10 nM of one of the following coagulation cascade factors: bovine factor VII (BfVII, Enzyme Res. Labs, South Bend, Ind.), bovine factor IX (BfIX, Enzyme Res. Labs.), bovine factor X (BfX, Enzyme Res. Labs), human factor X (HfX, gift of Dr. Walter Kisiel, Univ. of New Mexico, Albuquerque, N. Mex.), bovine factor Xa (BfXa, restriction grade-free of other proteins or protease activity, Boehringer-Mannheim, Indianapolis, Ind.), human protein S (HPS, Enzyme Res. Labs), and bovine protein C (BPC, Enzyme Res. Labs). At the end of the incubation, the cultures were washed twice with DMEM and pulsed for two hours in $^3$H-thymidine (1 μCi/ml) in DMEM containing 0.1% BSA. The cells were washed twice with cold phosphate buffered saline (PBS), treated twice with 5% trichloroacetic acid (TCA) for 5 min., dissolved with 0.25N NaOH (0.4 ml) incubated at 37° C. for 60 min., mixed with 5 ml Ecolume (ICN Biomedicals, Costa Mesa, Calif.), and their radioactivity determined in a scintillation counter. All assays were in triplicate. Error bars represent the standard error of the mean (S.E.M. with n=6 or more experiments). Smooth muscle cell mitogenic activity produced by exogenous agents is expressed as % relative mitogenic activity which is defined as:

$$\frac{(^3\text{H-thymidine incorp. exp. cpd.}) - (^3\text{H-thymidine incorp. control})}{^3\text{H-thymidine control}} \times 100$$

PDGF-BB is considered a good mitogen for smooth muscle cells.

Figure 1:
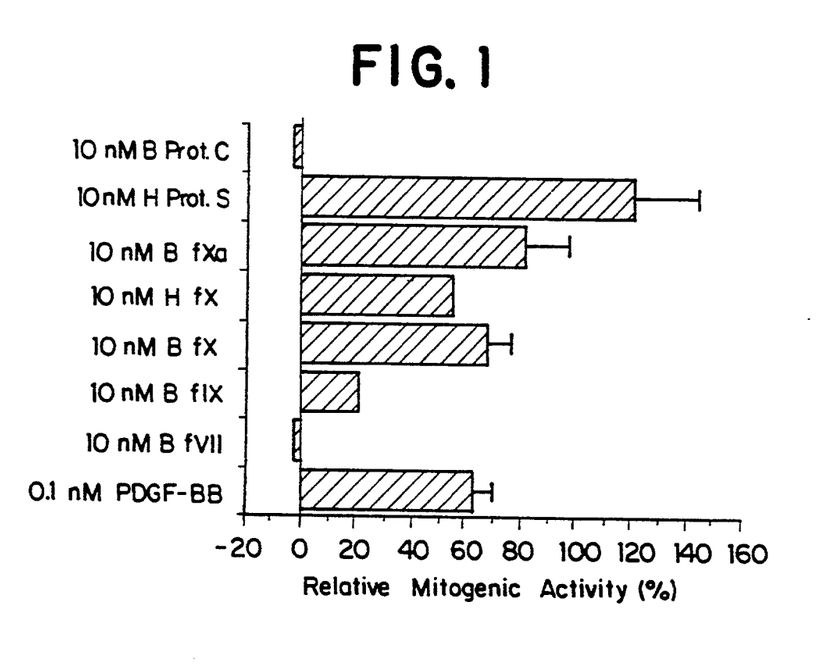
FIG. 1 shows a bar graph of the relative mitogenic activity of the blood coagulation cascade factors tested in Example 4.

The tested proteins share several conserved domains, amongst them are variable numbers of epidermal growth factor-like repeats. Factor X (fX, bovine and human), Xa (fXa, bovine) and protein S (PS, human) effectively stimulate DNA synthesis in primary cultures of smooth muscle cells as compared to platelet derived growth factor-BB. As shown in FIG. 1, platelet derived growth factor BB had relative mitogenic activity of about 63% above control mitogenic activity; whereas protein S had relative mitogenic activity of about 122% above control mitogenic activity values, Factor Xa about 82%, human factor X about 58%, and bovine factor X about 70% relative mitogenic activity above control values, respectively. Factor IX is only weakly mitogenic, whereas factor VII and protein C were inactive in the smooth muscle assay. Cell counts between 24 and 48 hours of smooth muscle cell incubation with the mitogens confirmed that 3H-thymidine incorporation is a fair index of cell division. In contrast, similar concentrations of factor Xa added to calf skin fibroblasts or to an SV-40 transformed smooth muscle cell line failed to produce a marked increase in mitosis. These results rule out contaminating fibroblasts as contributors to the observed mitogenic response.

As 40% of protein S occurs in free form and 60% as a C4b protein complex human plasma, the mitogenic activity of protein S which contained a significant fraction of protein S-C4b protein complex and found no apparent difference in mitogenic activity between the free and complex containing firms. Smooth muscle cell division stimulated by these coagulation factors is obtained with concentrations below circulating human plasma levels for factor X (178 nM), factor IX (89 nM), and protein S (278 nM).

From one primary culture preparation to another, some degree of variation was observed in the mitogenic response obtained with a given concentration of coagulation factor. Likewise, the percentage of cells which immunostained positive for alpha-actin, a resting state smooth muscle cell marker, also varied (60–80%) with each preparation. Despite the quantitative differences observed for DNA synthesis for disparate smooth muscle cell preparations, a consistent mitogenic result is obtained with several of the coagulation factors.

To rule out that a contaminant in the coagulation factor preparations were the smooth muscle cell mitogen, affinity-purified rabbit antibody to human factor X was used to deplete factor X and factor Xa preparations prior to assay with smooth muscle cells. No mitogenic activity remained.

EXAMPLE 5

Effect of Antistasin and Tick Anticoagulant Peptide on Factor Xa Induced Mitogenesis of Smooth Muscle Cells The effects of antistasin and tick anticoagulant peptide on factor Xa induced mitogenesis of smooth muscle cells were tested using the method shown in Example 4. At confluency, cells were washed twice with DMEM and incubated at 37° C. for 24 hours in DMEM containing 0.1% bovine serum albumin (BSA) (control), or DMEM containing 0.1% bovine serum albumin (BSA) and 10 nM bovine factor Xa (Boehringer-Mannheim) alone or in combination with recombinant antistasin or recombinant tick anticoagulant peptide. Recombinant antistasin and recombinant tick anticoagulant peptide were prepared as in Example 4. Whether antistasin or tick anticoagulant peptide was added following factor Xa or preincubated with factor Xa and added to the smooth muscle cell cultures, the results were the same. At the end of the 24 hour incubation, 3H-thymidine incorporation into DNA was monitored and smooth muscle cell mitogenic activity was assessed as described in Example 4.

Figure 2:
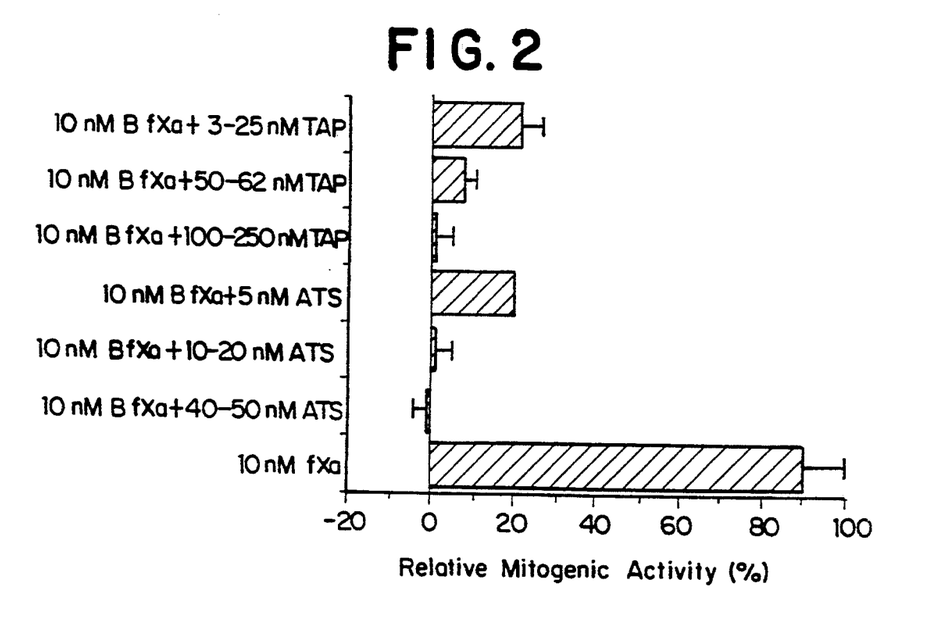
FIG. 2 shows a bar graph of the relative mitogenic activity of factor Xa, and factor Xa combined with antistasin or tick anticoagulant peptide.

As shown in FIG. 2, the relative mitogenic activity present with 10 nM fXa is about 88% above the control mitogenic activity. The relative mitogenic activity present with 10 nM fXa and 3–25 nM TAP is reduced significantly to about 25% above control values. A similar amount of relative mitogenic activity, about 23% above control values, was produced with 10 nM fXa and 5 nM antistasin (ATS). With 10 nM fXa and 50–62 nM TAP, the relative mitogenic activity was reduced even further to about 9% above control values. 10 nM fXa and 10–20 nM antistasin (ATS) produced even less relative mitogenic activity, about 2%. 10 nM fXa with 100–250 nM TAP and 10 nM fXa with 40–50 nM antistasin (ATS) produced relative mitogenic activities that were near zero. In FIG. 1, the vertical line at the top of each bar represents the S.E.M., where no bar is present, less then three experiments were performed.

Variation in the Factor Xa induced mitogenic response of different preparations of smooth muscle cell cultures was tested by comparing the results of mitogenesis assays performed according to the method in Example 4 on different preparations of rat aortic smooth muscle cells. Table 3 shows the results of two representative experiments using bovine factor Xa (restriction grade, Boehringer-Mannheim) and two different preparations of rat aortic smooth muscle cell. The mitogenesis assays were preformed in triplicate and less than 10% standard deviation was observed. The variation in the observed mitogenic response between smooth muscle cell culture passages of the same preparation was 10–30%.

TABLE 3

Variation in the Factor Xa Induced Mitogenic Response of Different Preparations of Smooth Muscle Cell (SMC) Cultures

| bovine fXa (nM) | % Relative Mitogenic Activity | |
|---|---|---|
| | SMC Prep A | SMC Prep B |
| 1 | 61 | 13 |
| 5 | 167 | 27 |
| 10 | 217 | 48 |
| 50 | 411 | 80 |

The recombinant antistasin and tick anticoagulant peptide were assayed for their ability to inhibit fXa by preincubating aliquots with fXAa (restriction grade, Boshringer Mannheim) before mixing with 100 microliters fXa deficient plasma and 100 microliters 25 nM $CaCl_2$ and the clotting time was determined.

EXAMPLE 6

Comparison of $^3$H-Thymidine Incorporation and Cell Proliferation in Rat Acttic Smooth Muscle Cell Cultures Rat smooth muscle cells were incubated with different blood coagulation factors to determine $^3$H-thymidine incorporation and effect cell number. Table 4 shows the results from a representative experiment comparing thymidine incorporation with cell proliferation in aortic smooth muscle cell cultures treated for 36 hours with or without two different coagulation factors. At the end of the incubation, half of the groups were pulsed with $^3$H-thymidine for two hours while their identically treated counterparts were dissociated with trypsin and the cells (smooth muscle cells on the basis of a reddish-brown staining pattern with Masson's trichome) were counted. Although there was not a direct correspondence between the per cent increase in thymidine incorporation and cell number, the increase in DNA synthesis correlated well with an increase in cell number. bovine factor Xa increased cell proliferation in a dose dependent manner. 10 mM Protein S induced greater cell proliferation than 50 mM bovine factor Xa.

TABLE 4

| Treatment | CPM Incorporated | SMC Number |
|---|---|---|
| Buffer | 4,710 ± 272 | $3.1 \times 10^5$ |
| 10 mM bovine factor Xa | 7,470 ± 368 | $4.5 \times 10^5$ |
| 50 mM bovine factor Xa | 14,709 ± 1,439 | $5.7 \times 10^5$ |
| 10 mM human protein S | 30,074 ± 2,837 | $6.5 \times 10^5$ |

EXAMPLE 7

Effect of Specific Factor Xa Inhibitors on Human Protein S and Bovine Factor X Induced Smooth Muscle Cell Mitogenesis The effects of antistasin and tick anticoagulant peptide on factor X and protein S induced mitogenesis of smooth muscle cells was tested using the method shown in Example 4. At confluency, cells were washed twice with DMEM and incubated at 37° C. for 24 hours in DMEM containing 0.1% bovine serum albumin (BSA) (control), DMEM containing 0.1% bovine serum albumin (BSA) and 10 nM bovine factor X (Boehringer-Mannheim) or protein S alone, or in combination with recombinant antistasin or recombinant tick anticoagulant peptide. At the end of the 24 hour incubation, $^3$H-thymidine incorporation into DNA was monitored and smooth muscle cell mitogenic activity was assessed as described in Example 4.

Figure 3:
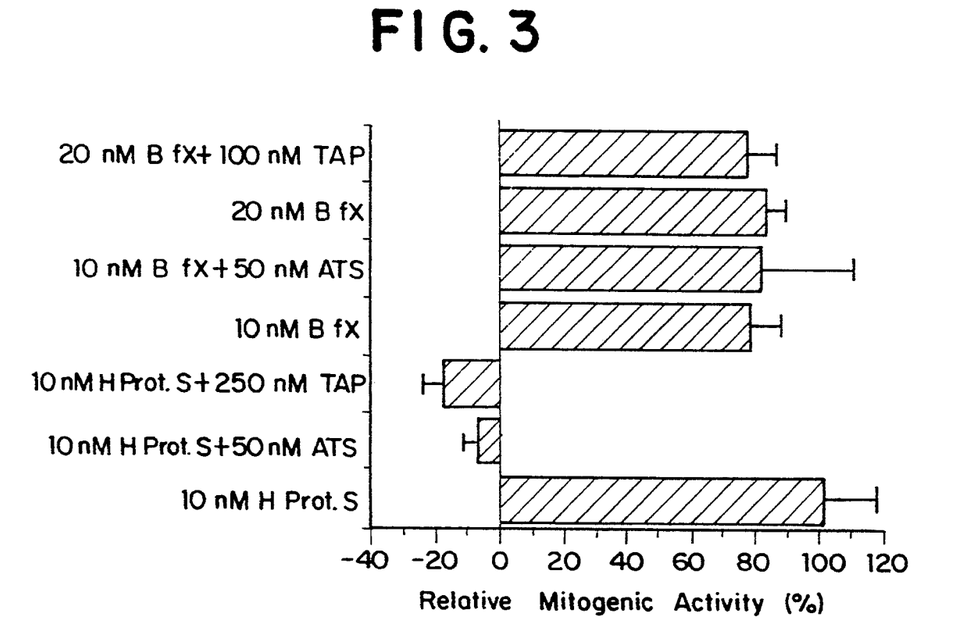
FIG. 3 shows a bar graph of the relative mitogenic activity of factor X, factor X combined with antistasin or tick anticoagulant peptide, protein S, and protein S combined with antistasin or tick anticoagulant peptide.

FIG. 3 illustrates the average mitogenic activity and SEM of smooth muscle cells incubated with human protein S or bovine factor X in the absence and presence of specific factor Xa inhibitors. As shown in FIG. 3, the relative mitogenic activity of bovine factor X is not significantly inhibited by 100 nM tick anticoagulant peptide (TAP), or 50 nM antistasin (ATS). The relative mitogenic activity of protein S (Prot S), however, is abolished by 250 nM TAP or 50 nM antistasin.

We claim:

1. A method of inhibiting proliferation of smooth muscle cells in the wall of a blood vessel comprising the step of:
   administering to an individual who has undergone balloon angioplasty, percutaneous translumninal coronary angioplasty or cardiac transplantation, a compound capable of inhibiting blood factor Xa in an amount effective to inhibit proliferation of said smooth muscle cells, said compound selected from the group consisting of antistasin and tick anticoagulant peptide.

2. The method of claim 1 wherein said compound is antistasin.

3. The method of claim 1 wherein said compound is tick anticoagulant peptide.

4. The method of claim 1 wherein said individual has undergone balloon angioplasty.

5. The method of claim 1 wherein said individual has undergone percutaneous transluminal coronary angioplasty.

6. The method of claim 1 wherein said individual has undergone coronary transplantation.

7. A method of treating an atherosclerotic lesion wherein said lesion comprises smooth muscle cells, comprising the step of:
   administering to an atherosclerotic lesion a compound capable of inhibiting blood factor Xa in an amount effective to inhibit proliferation of smooth muscle cell proliferation, said compound selected from the group consisting of antistasin and tick anticoagulant peptide.

8. The method of claim 7 wherein said compound is antistasin.

9. The method of claim 7 wherein said compound is tick anticoagulant peptide.

10. The method of claim 7 wherein said individual has undergone a surgical treatment selected from the group consisting of: balloon angioplasty, percutaneous transluminal coronary angioplasty and cardiac transplantation.

11. The method of claim 7 wherein said individual has undergone balloon angioplasty.

12. The method of claim 7 wherein said individual has undergone percutaneous transluminal coronary angioplasty.

13. The method of claim 7 wherein said individual has undergone coronary transplantation.

14. A method of treating narrowing of the lumen of a blood vessel wherein said narrowing is due at least in part to hyperplasia of smooth muscle cells in the wall of said blood vessel comprising the step of:
   administering to a blood vessel having narrowing of the lumen that is due at least in part to hyperplasia of smooth muscle cells in the wall of said blood vessel, a compound capable of inhibiting blood factor Xa in an amount effective to inhibit proliferation of smooth muscle cells in said blood vessel wall to thereby increase the size of the lumen of the blood vessel, said compound selected from the group consisting of antistasin and tick anticoagulant peptide.

15. The method of claim 14 wherein said compound is antistasin.

16. The method of claim 14 wherein said compound is tick anticoagulant peptide.

17. The method of claim 14 wherein said individual has undergone a surgical treatment selected from the group consisting of: balloon angioplasty, percutaneous transluminal coronary angioplasty and cardiac transplantation.

18. The method of claim 14 wherein said individual has undergone balloon angioplasty.

19. The method of claim 14 wherein said individual has undergone percutaneous transluminal coronary angioplasty.

20. The method of claim 14 wherein said individual has undergone coronary transplantation.

* * * * *

UNITED STATES PATENT AND TRADEMARK OFFICE
CERTIFICATE OF CORRECTION

PATENT NO. : 5,385,885
DATED : January 21, 1995
INVENTOR(S) : Gregory P. Gasic, Gabriel J. Gasic, Tatiana B. Gasic It is certified that error appears in the above-indentified patent and that said Letters Patent is hereby corrected as shown below:

Column 16, line 7, insert -- identifying an individual at risk of an injury in the wall of a blood vessel --.

Column 16, line 28, insert -- identifying said individual suffering from said atherosclerotic lesion --.

Column 16, line 54, insert -- identifying said individual suffering from narrowing of the lumen of a blood vessel; --.

Signed and Sealed this

Twenty-second Day of August, 1995

Attest:

BRUCE LEHMAN

*Attesting Officer*     *Commissioner of Patents and Trademarks*